United States Patent [19]

Felix

[11] 4,220,656
[45] Sep. 2, 1980

[54] 7,7-DICHLORO-BICYCLOHEPTANE IMIDE COMPOUNDS AND THEIR USE AS BIOCIDES

[75] Inventor: Raymond A. Felix, Richmond, Calif.

[73] Assignee: Stauffer Chemical Company, Westport, Conn.

[21] Appl. No.: 3,572

[22] Filed: Jan. 15, 1979

[51] Int. Cl.² .................... A61K 31/40; C07D 209/48
[52] U.S. Cl. ................ 424/274; 260/326 C; 260/326 H
[58] Field of Search ............. 260/326 C, 326 H; 424/274

[56] References Cited

U.S. PATENT DOCUMENTS 4,087,540  5/1978  Sandermann et al. ........... 260/326 C

FOREIGN PATENT DOCUMENTS 738998  7/1966  Canada ............................ 260/326 H
40-21620  9/1965  Japan ............................. 260/326 C

OTHER PUBLICATIONS

Chemical Abstracts 66:27982w (1967), Bridged Ring Phthalimides as Fungicides.

Primary Examiner—Donald G. Daus
Assistant Examiner—M. C. Eakin
Attorney, Agent, or Firm—Joel G. Ackerman

[57] ABSTRACT

Novel compounds having the formula

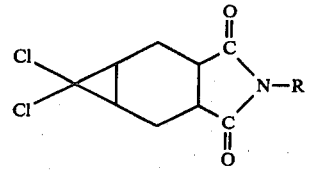

in which R is thio(halo-lower alkyl) or 3,4-dichlorophenyl, having bactericidal and/or fungicidal properties.

9 Claims, No Drawings

7,7-DICHLORO-BICYCLOHEPTANE IMIDE COMPOUNDS AND THEIR USE AS BIOCIDES

This invention relates to novel compounds having the formula

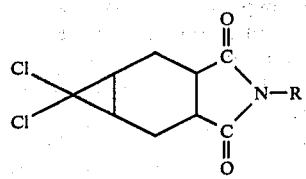

in which R is thio(halo-lower alkyl) or 3,4-dichlorophenyl. As will be seen from the data hereinafter, these compounds possess activity against certain fungi and bacteria.

By the term "lower alkyl" is meant saturated acyclic substituents of this type having from 1 to 4 carbon atoms. The term "halo" is intended to include fluoro, chloro, bromo and iodo and may include one or several types of halogens substituted on a particular lower alkyl moiety. Preferred embodiments of this substituent are fluoro and/or chloro.

A general method of preparation of the compounds of the present invention is as follows.

A diester of a tetrahydrophthalic acid is condensed with dichlorocarbene to form a bicyclo[4.1.0] heptane. The ester group can then be hydrolyzed to the diacid which can then be converted to the anhydride by treating with a conventional dehydrating agent, for example acetyl chloride. The anhydride is then converted to an imide by reaction with a source of ammonia, such as urea. The compounds of this invention can be prepared by condensing the imide with a sulfenyl chloride in the presence of a base, for instance, triethylamine.

The following is a representative example of a compound of this invention.

Preparation of N-(trichloromethyl-thio)bicyclo [4.1.0]heptane-7,7-dichloro-3,4-dicarboxylic acid imide (Compound No. 1 herein).

(a) There were placed in a flask 126 grams of 4,5-dicarboethoxy cyclohexene, 100 milliliters of chloroform and 5 grams of tetrabutyl phosphonium chloride. To the resulting solution there was added 110 milliliters of a 50% aqueous solution of sodium hydroxide. The addition was carried out over a three-hour period; the mixture was then stirred for an additional three hours. There were then added 150 milliliters of water and 80 milliliters of a 50% aqueous solution of sodium hydroxide; the mixture was stirred for several more hours. Water was added to dissolve the solids and the solution was washed once with chloroform. The aqueous layer was then acidified with concentrated hydrochloric acid and extracted with methylene chloride. The methylene chloride was dried and evaporated to yield 62 grams of a tan solid, identified as bicyclo[4.1.0]heptane-7,7-dichloro-3,4-dicarboxylic acid.

(b) In a flask were placed 5.5 grams of the dicarboxylic acid prepared in step (a) above and 10 milliliters of acetyl chloride. The solution was heated to reflux for 15 minutes. The reaction mixture was then evaporated at a high vacuum to yield 4.7 grams of a tan solid identified as the anhydride of the acid prepared in step (a).

(c) In a flask were placed 4.7 grams of the anhydride prepared in step (b) above, 1.2 grams of urea and 10 milliliters of acetic acid. The mixture was refluxed for 1½ hours, then allowed to cool. Methylene chloride was then added and the organic layer washed with water and then eith a 5% aqueous solution of potassium carbonate. The organic layer was then dried and the solvent evaporated to yield 3 grams of a tan solid, identified as the imide of the carboxylic acid in step (a).

(d) In a flask were placed 2.4 grams of the imide prepared in step (c) above, 1.1 grams of triethylamine and 10 milliliters of methylene chloride. To this solution was added 1.9 grams of perchloromethylmercaptan, dissolved in 5 milliliters of methylene chloride. The reaction mixture was then stirred for several hours, following which 100 milliliters of methylene chloride was added and the solution washed with water. The organic layer was separated, dried and the solvent stripped to yield 3.8 grams of a tan solid, melting point 140°–155° C. identified as N-(trichloromethylthio)bicyclo[4.1.0]heptane-7,7-dichloro-3,4-dicarboxylic acid imide.

The following Table I contains representative examples of compounds of the present invention.

Identification of the compounds produced in steps (a)–(d) above and in Table I was performed by infrared, nuclear magnetic resonance and mass spectroscopic techniques.

TABLE I

| Compound No. | R | m.p., °C. |
|---|---|---|
| 1 | SCCL₃ | 140–155 |
| 2 | SCCl₂CCl₂H | 161–164 |
| 3 | (3,4-dichlorophenyl) | (semi-solid) |
| 4 | SCCl₂CCl₂F | (crude solid) |

Fungicidal and Bactericidal Evaluation

The compounds in Table I above were tested for fungicidal and bactericidal activity by the following procedures.

In Vitro Vial Tests

Tubes of sterilized nutrient and malt extract broth were prepared. Aliquots of the toxicant, dissolved in an appropriate solvent, were injected through the stopper, into the broth, to provide concentrations ranging from 50 ppm downward. The test organisms consisted of two fungi, *Aspergillus niger* (A.n.) van Tieghem and *Penicillium italicum* (P.i.) Wehmer, and three bacteria, *Escherichia coli* (E.c.) Migula, *Staphylococcus aureus* (S.a.) Rosenbach and *Erwinia amylovora* (E.a.), (Burill) Sinslow, et al. Three drops of a spore suspension of each of the fungi were injected into the tubes of malt broth and three drops of the bacteria were injected into the nutrient broth. One week later the growth of each organism was observed and effectiveness of the chemical was recorded as the lowest concentration in ppm which provided 100% inhibition of growth as compared to untreated inoculated tubes.

The results of these tests are found in Table II.

TABLE II

| Compound No. | (Values in ppm) | | | | |
|---|---|---|---|---|---|
| | A.n. | P.i. | E.c. | S.a. | E.a. |
| 1 | 5 | 5 | >50 | 5 | 10 |
| 2 | 1 | 1 | >50 | 10 | >50 |
| 3 | >50 | >50 | >50 | 0.5 | >50 |
| 4 | 5 | 1 | >50 | 25 | 25 |

Foliar Preventative Sprays

Bean Rust

The chemicals were dissolved in an appropriate solvent and diluted with water containing several drops of a wetting agent. Test concentrations, ranging from 1000 ppm downward, were sprayed to run-off on the primary leaves of pinto beans (*Phaseolus vulgaris L.*). After the leaves were dried, they were inoculated with a water suspension of spores of the bean rust fungus (*Uromyces phaseoli* Arthur) and the plants were placed in an environment of 100% humidity for 24 hours. The plants were then removed from the humidity chamber and held until disease pustules appeared on the leaves. Effectiveness was recorded as the lowest concentration, in ppm, which provided 75% or greater reduction in pustule formation as compared to untreated, inoculated plants.

Bean Powdery Mildew

Test chemicals were prepared and applied in the same manner as for the bean rust test. After the plants were dry, the leaves were dusted with spores of the powdery mildew fungus (*Erysiphe polygoni* De Candolle) and the plants were retained in the greenhouse until the fungal growth appeared on the leaf surface. Effectiveness was recorded as the lowest concentration, in ppm, which provided 75% or greater reduction in mycelial growth on the leaf furface as compared to untreated, inoculated plants.

Tomato Early Blight

Test chemicals were prepared and applied in the same manner as the bean rust and powdery mildew tests except that 4-week old tomato (*Lycopersicon esculentum*) plants were utilized as the host plant. When the leaves were dry, they were inoculated with a water suspension of spores of the early blight fungus (*Alternaria solani* Ellis and Martin) and placed in an environment of 100% humidity for 48 hours. The plants were then removed from the humidity chamber and held until disease lesions appeared on the leaves. Effectiveness was recorded as the lowest concentration, in ppm, which provided 75% or greater reduction in the number of lesions formed as compared to untreated, inoculated plants.

Bluegrass leaf spot

The test chemicals were dissolved in an appropriate solvent and further diluted with a 50:50 acetone:water solution. "Marion" Kentucky Bluegrass plants (*Poa pratensis* L.), approximately four weeks old, were sprayed to the point of run-off with the test solutions. Test concentrations ranged from 1000 ppm downwards. After the leaves dried, they were inoculated with a water suspension of *Helminthosperium sativum* Tammel and held in a greenhouse at 27° C. until disease lesions appeared on the leaves. Effectiveness was recorded as the lowest concentration in ppm which provided 75% or greater reduction in the number of lesions as compared to untreated inoculated plants.

Foliar Eradicative Sprays

Bean Rust

Untreated bean plants were inoculated with spores of the bean rust fungus and placed in an environment of 100% humidity for 24 hours. They were then removed from the humidity chamber and held in the greenhouse for two days to allow the disease to become established. The test chemicals were then prepared and applied in the same manner as in the preventative spray tests. Eradicative effectiveness was recorded as the lowest concentration, in ppm, which provided 75% or greater reduction in pustule formation as compared to untreated inoculated plants.

Bean Powdery Mildew

Untreated pinto bean plants were dusted with spores of the powdery mildew fungus and maintained in the greenhouse until mycelial growth appeared on the leaf surface. Test chemicals were then prepared and applied in the same manner as for the preventative spray test. Four days later, the leaves were examined for inhibition of further mycelial growth. Eradicative effectiveness was recorded as the lowest concentration, in ppm, which provided 75% or greater reduction in mycelial growth on the leaf surface as compared to untreated inoculated plants.

Tube Systemic Test

Bean Rust

The chemicals were dissolved in an appropriate solvent and diluted with tap water to a series of descending concentrations beginning at 50 ppm. Sixty milliliters of each concentration was placed in a test tube. A pinto bean plant was placed in each tube and supported with a piece of cotton so that only the roots and lower stem were in contact with the test solution. Forty-eight hours later the bean leaves were inoculated with a water suspension of spores of the bean rust fungus and placed in an environment with 100% humidity for 24 hours. The plants were then removed from the humidity chamber and maintained in the greenhouse until the disease pustules appeared on the leaves. Effectiveness was recorded as the lowest concentration, in ppm, which provided 75% or greater reduction in pustule formation as compared to untreated, inoculated plants.

Bean Powdery Mildew

Test chemicals were prepared and applied in the same manner as for the bean rust systemic test. After two days, the leaves were dusted with spores of the powdery mildew fungus and maintained in the greenhouse until mycelial growth appeared on the leaf surfaces. Effectiveness was recorded as the lowest concentration, in ppm, which provided 75% or greater reduction in mycelial growth on the leaf surface as compared to untreated, inoculated plants.

The results of the various evaluations are contained in Tables IIIA–IIIC which follow:

TABLE IIIA

| | Foliar Preventative Tests (ppm) | | | |
|---|---|---|---|---|
| Compound No. | Bean Rust | Powdery Mildew | Tomato Blight | Leaf Spot |
| 1 | 500 | 100 | 500 | 1000 |
| 2 | 100 | >1000 | >1000 | 500 |
| 3 | >1000 | >1000 | — | — |

TABLE IIIA-continued

| | Foliar Preventative Tests (ppm) | | | |
|---|---|---|---|---|
| Compound No. | Bean Rust | Powdery Mildew | Tomato Blight | Leaf Spot |
| 4 | 100 | >1000 | 500 | 500 |

TABLE III B

| | Foliar Eradicative Tests (ppm) | |
|---|---|---|
| Compound No. | Bean Rust | Powdery Mildew |
| 1 | — | 1000 |
| 2 | >1000 | — |
| 3 | — | — |
| 4 | >1000 | — |

TABLE III C

| | Systemic Tests (ppm) | |
|---|---|---|
| Compound No. | Bean Rust | Powdery Mildew |
| 1 | >50 | >50 |
| 2 | >50 | — |
| 3 | >50 | — |
| 4 | >50 | — |

The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are normally found in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite, diatomite; gypsum; clays, propellants such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as by light, or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise between about 0.01 and about 80% by weight of the composition.

What is claimed is:

1. A compound having the formula

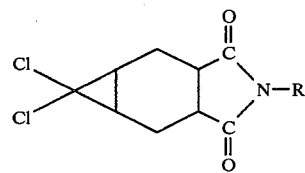

in which R is thio(halo-lower alkyl) or 3,4-dichlorophenyl.

2. A compound according to claim 1 in which R is trichloromethylthio.

3. A compound according to claim 1 in which R is 1,1,2,2-tetrachloroethylthio.

4. A compound according to claim 1 in which R is 3,4-dichlorophenyl.

5. A compound according to claim 1 in which R is 1,1,2,2-tetrachloro,2-fluoroethylthio.

6. A method of controlling fungi comprising applying to the fungi or the locus thereof a fungicidally effective amount of a compound having the formula

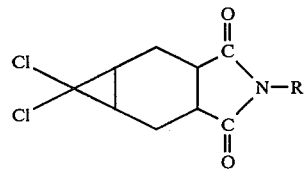

in which R is thio(halo-lower alkyl).

7. A compound according to claim 6 in which the compound is applied prior to the emergence of fungi at the locus.

8. A method of controlling bacteria selected from the group consisting of *Staphylococcus aureus* and *Erwinia amylovora* comprising applying to the bacteria or the locus thereof a bactericidally effective amount of a compound having the formula

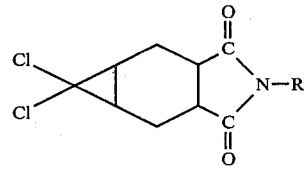

in which R is thio(halo-lower alkyl) or 3,4-dichlorophenyl.

9. A fungicidal or bactericidal composition of matter comprising a fungicidally or bactericidally effective amount of a compound having the formula

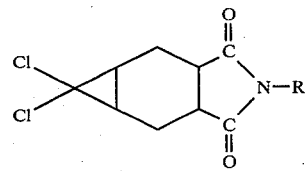

in which R is thio(halo-lower alkyl) or 3,4-dichlorophenyl, and a biocidally suitable inert carrier or diluent.

* * * * *

UNITED STATES PATENT AND TRADEMARK OFFICE
CERTIFICATE OF CORRECTION

PATENT NO. : 4,220,656
DATED : September 2, 1980
INVENTOR(S) : Raymond A. Felix

It is certified that error appears in the above—identified patent and that said Letters Patent is hereby corrected as shown below:

Column 2, Table I, Compound 1 under the heading "R"

"SCCL$_3$" should read -- SCCl$_3$ --.

Column 6, line 34 (Claim 7), "compound" should read

-- method --.

Signed and Sealed this

Eighth Day of December 1981

[SEAL]

Attest:

Attesting Officer

GERALD J. MOSSINGHOFF
Commissioner of Patents and Trademarks